US007393521B2

(12) United States Patent
Hruza

(10) Patent No.: US 7,393,521 B2
(45) Date of Patent: Jul. 1, 2008

(54) IN SITU REMEDIATION OF WASTE IN FARM ANIMAL BEDDING SUBSTRATES

(75) Inventor: Sandra Hruza, The Woodlands, TX (US)

(73) Assignee: Bionutratech, Inc., Shell Knob, MO (US)

( * ) Notice: Subject to any disclaimer, the term of this patent is extended or adjusted under 35 U.S.C. 154(b) by 784 days.

(21) Appl. No.: 10/781,561

(22) Filed: Feb. 18, 2004

(65) Prior Publication Data

US 2005/0180944 A1 Aug. 18, 2005

(51) Int. Cl.
*A61L 11/00* (2006.01)

(52) U.S. Cl. ...................... 424/76.6; 119/171; 424/76.8; 424/409; 424/411; 424/420; 424/613; 424/648

(58) Field of Classification Search ....................... None
See application file for complete search history.

(56) References Cited

U.S. PATENT DOCUMENTS 4,251,255 A * 2/1981 Wagner et al. ................. 71/27
4,294,821 A 10/1981 Neumiller
4,435,431 A 3/1984 Akatsuka
5,207,830 A * 5/1993 Cowan et al. ............... 106/672
5,443,845 A 8/1995 Felix
5,574,093 A * 11/1996 States et al. .............. 514/772.1
5,670,677 A 9/1997 Ponsati Obiols et al.
5,725,885 A 3/1998 Felix et al.
5,951,946 A 9/1999 Eaton et al.
5,954,868 A 9/1999 Felix et al.
6,277,279 B1 8/2001 Hruza
6,436,423 B1 8/2002 Ballinger, Jr. et al.

FOREIGN PATENT DOCUMENTS

EP 0288633 * 11/1988
EP 0620014 * 10/1994

* cited by examiner

*Primary Examiner*—Neil Levy
(74) *Attorney, Agent, or Firm*—Jeffrey L. Streets; Streets & Steele

(57) ABSTRACT

Composition and method for promoting growth of microbes that are capable of degrading animal waste. The method includes applying a nontoxic composition to a bedding substrate that is disposed to receive animal waste. The composition comprises a carboxylic acid, preferably the carboxylic acid is a fatty acid, and more preferably a combination of a saturated fatty acid and an unsaturated fatty acids. Specifically, a preferred composition comprises a saturated fatty acid having from 12 to 22 carbon atoms and an unsaturated fatty acid having from 12 to 22 carbon atoms. A still more preferred composition used both saturated and unsaturated fatty acids having from 16 to 20 carbon atoms. Optionally, the composition may include or encapsulate nutrients, an oxygen-releasing compound, or microbes.

32 Claims, No Drawings

IN SITU REMEDIATION OF WASTE IN FARM ANIMAL BEDDING SUBSTRATES

BACKGROUND OF THE INVENTION

1. Field of the Invention

This invention relates to the in situ treatment of bedding substrates that are exposed to live farm animals and their waste products.

2. Background of the Related Art

Domestic farm animals, such as chickens, dairy cows, horses, sheep, goats, and pigs, are often kept on a bedding material that can absorb or cover much of their own feces and urine to prevent undue contact with the animals. The use of the bedding may be continuous, such as in the typical six-week growth period of chickens in grow houses, or only for special purposes, such as when livestock are taken into a barn from the field. Depending upon availability and the type of animal, these bedding materials may include wood shavings, wood chips, wood pellets, sawdust, straw and sand.

However, as the bedding material receives an increasing load of animal waste and the waste remains in the bedding material for an extended period of time, the odors produced from the bedding layer become very strong. In fact, one of the odorous gases is ammonia, which is blamed for irritating or burning the throats of the chickens and causes them to eat less of their feed and perhaps become more susceptible to infection and disease.

Most odors identified as objectionable to human beings are the result of volatile compounds generated or liberated during the decomposition of manure. Odorous compounds may be a result of biological reactions occurring primarily in an anaerobic environment because many of the odorous compounds commonly found in fresh manure become more concentrated during anaerobic decomposition. Some of the odors emanating during the decomposition of manure may also be the result of biological processes carried out during aerobic decomposition.

Odors originating from manure are a result of a broad range of odor producing compounds. Commonly reported odorous compounds associated with manure and waste water are gases which are released from the manure during decomposition. Examples of these gases include sulfur-containing gases such as hydrogen sulfide, nitrogen-containing gases in the amine form such as ammonia, mercaptans, volatile organic acids, phenols, and alcohols. Some of these odorous compounds have determinable points at which the odors affect human beings. For example, ammonia present at a concentration of 10 ppm may cause irritation to eyes and nose, and hydrogen sulfide present at a concentration of 10 ppm is toxic and may cause headaches, dizziness, nausea, unconsciousness, and death. The wide range of odorous compounds from manure increase the complexity of odor control solutions.

Poultry raised commercially by intensive farming methods use high-density growth conditions that can transmit disease through the poultry house and, more particularly, the bedding. The poultry house bedding is a substrate for the poultry to stand on and provides a natural target for pecking. In addition, birds peck the bedding as they would naturally peck the ground in search of food and grit for their gizzard. Grit is used in a bird's gizzard as a means to grind food. As birds ingest waste products that have been deposited throughout the poultry house, and particularly in the bedding, certain pathogenic organisms such as bacteria, viruses and parasites are introduced into the bird's digestive system. As an example, the common disease coccidiosis is transmitted from bird to bird through feces that is mingled with the bedding and then ingested by the birds. It is also known in the industry that ingestion of bedding by commercially raised poultry is a common source of several other diseases caused by pathogens such as Salmonella, Clostridia and other endoparasites, viruses and bacteria.

Presently, treatment for such diseases includes the addition of anticoccidials and any other medications to feed and/or water for the treatment and/or prevention of such specific pathogen-based diseases. Other common medications for such diseases include antibiotics such as, for example, ionophores, which include Salinomycin and Monensin.

However, there remains a need for improved methods of treating farm animal bedding materials and the waste products deposited on the bedding materials. It would be greatly desirable if the method would eliminate the offensive odors associated with farm animal waste. It would also be desirable if the method improved the health of the animals, such as by reducing the presence of pathogenic bacteria, and improved the performance and efficiency of the animal farming operation. It would be further desirable if the method did not require any major changes to existing farm practices.

SUMMARY OF THE INVENTION

The present invention provides a method for treating animal bedding waste characterized in that the avian performance is increased. This method includes applying to an animal bedding material between about 0.025 and about 6 pounds of a composition per cubic yard of the animal bedding material, wherein the composition comprises at least 5 weight percent of carboxylic acids having from 12 to 22 carbon atoms, preferably between 16 and 20 carbon atoms. An exemplary method includes applying between about 0.025 and about 2 pounds of the composition for each cubic yard of the substrate every 1 to 3 weeks. Preferably, the composition includes between 0.025 and 0.6 pounds of carboxylic acids per cubic yard of substrate. The method may further include moistening the bedding with water.

The carboxylic acids preferably include one or more fatty acids selected from saturated fatty acids (such as stearic acid, palmitic acid and mixtures thereof), unsaturated fatty acids (such as oleic acid, linoleic acid and mixtures thereof), and combinations thereof. In one embodiment, the one or more fatty acids include a combination of saturated and unsaturated fatty acids and the ratio of the saturated fatty acids to the unsaturated fatty acids is between 70:30 and 30:70 by weight, or between about 60:40 and 40:60. Preferably, the saturated fatty acids consist essentially of stearic acid and the unsaturated fatty acids consist essentially of oleic acid, linoleic acid, or a combination thereof.

The composition may further comprise additives, such as at least 1 weight percent of an amine-substituted form of a fatty acid. Another suitable additive is a source of molecular oxygen. For example, the source of molecular oxygen may be selected from calcium peroxide, hydrogen peroxide, urea hydrogen peroxide, sodium percarbonate, potassium peroxide, and magnesium peroxide. Furthermore, if the source of molecular oxygen is included, it preferably comprises between about 1 and 20 percent by weight of the one or more fatty acids. Yet another additive is between about 0.1 and about 2 weight percent of amorphous silica mixed with the solids of the composition to prevent clumping of the material. Still further, nutrients, such as nitrogen, phosphorus, iron, potassium and combinations thereof, may be included in the composition.

Preferably, the one or more fatty acids are solids at ambient temperatures and are provided in the form of pellets, powders, granules, or cakes, but most preferably powders. The animal bedding is selected from sawdust, wood chips, wood shavings, straw, hay, rice hulls, and sand.

A bedding for animals is provided comprising a layer of a substrate selected from wood shavings, wood chips, wood pellets, sawdust, straw, hay, sand, and combinations thereof, and a composition comprising one or more carboxylic acid contacting the substrate, wherein between about 0.025 and about 6 pounds of the composition is provided for each cubic yard of the substrate. Preferably, the composition further comprises one or more nutrients selected from nitrogen, phosphorous, iron, potassium, and combinations thereof.

Also provided is a method for treating animal bedding waste. The method comprises applying fatty acids having from 12 to 22 carbon atoms to an animal bedding material, wherein the fatty acids are applied in an amount that is effective to enhance remediation of animal waste within the bedding material. Preferably, the amount is also effective to reduce odors from the animal bedding waste. Suitably, the fatty acids may have from 16 to 20 carbon atoms.

Another embodiment of the invention provides a method of poultry farming. The method includes applying an effective amount of a powder composition comprising at least 5 weight percent of carboxylic acids having from 12 to 22 carbon atoms to a layer of bedding material selected from wood shavings, wood chips, wood pellets, sawdust, hay, sand, and combinations thereof. The method also includes growing a batch of poultry on the bedding material for a period of at least five weeks, wherein the layer of bedding material receives manure and urine from the poultry at least periodically throughout the period. Alternatively, this method may include the use of any of the compositions disclosed herein. Preferably, the step of applying an effective amount of a powder composition includes applying between about 0.025 and about 6 pounds of the powder composition per cubic yard of bedding material every 1 to 3 weeks. More preferably, between about 0.025 and about 2 pounds of carboxylic acids is applied for each cubic yard of the substrate every 1 to 3 weeks.

The method of poultry farming may further includes any one or more of the following steps: moistening the animal bedding material; agitating the animal bedding material; applying the composition by mixing the composition with water and spraying the mixture over the bedding material; reapplying the powder composition to the bedding at least once during the period; growing another batch of poultry on the same bedding material for a second period of at least five weeks; and removing the used bedding material, wherein the removal can include disposal or reuse as a fertilizer.

DETAILED DESCRIPTION OF PREFERRED EMBODIMENTS

The present invention provides a method for promoting growth of microbes that are capable of degrading organic material. The method includes applying a nontoxic composition to an animal bedding substrate, wherein the composition comprises a carboxylic acid, preferably the carboxylic acid is a fatty acid, and more preferably a combination of a saturated fatty acid and an unsaturated fatty acids. Specifically, a preferred composition comprises a saturated fatty acid having from 12 to 22 carbon atoms and an unsaturated fatty acid having from 12 to 22 carbon atoms. A still more preferred composition used both saturated and unsaturated fatty acids having from 16 to 20 carbon atoms. Because the unsaturated fatty acids tend to be in the liquid phase at room temperature, it is preferred to provide the combination of saturated and unsaturated fatty acids together to form a solid particulate at room temperature and that will remain a solid even at elevated ambient temperatures. Optionally, an oxygen-releasing compound may be included in the composition.

It should be recognized that the compositions described for application to the bedding materials do not generally include microbes and that the preferred bioremediation process may be referred to as biostimulation. Applying these compositions, the growth of microbes, whether indigenous or separately applied, is stimulated or enhanced by providing appropriate compounds and conditions. Alternatively, the compositions may in fact include microbes, such as non-indigenous or engineered microbes, to participate in the bioremediation process that may be referred to as bio augmentation. It should be recognized that the non-indigenous microbes may be the same or similar to the indigenous microbe, but are provided along with the compositions.

The animal bedding or substrate material is preferably a natural organic material, such those based on cellulose—the main constituent of the structure of plants. Examples of suitable natural organic materials include sawdust, wood chips, wood shavings, rice hulls, and hay or straw. Hay is made from forage plants that have been cut and dried. Sawdust is a collection of wood fragments made by a saw in cutting. The exact structure of the substrate or the manner of making the substrate is not deemed to be of critical importance.

The success or effectiveness of bioremediation is generally dependent upon certain key factors being present nearly simultaneously. First, the presence of organic degrading microorganisms, either indigenous or not. Second, there should be oxygen and water available to permit the microorganisms to be metabolically active. Third, there must also be available sufficient quantities of biologically utilizable nutrients, such as nitrogen and phosphorous compounds, to enable the microbial population to rapidly metabolize the available organic materials.

Microorganisms capable of degrading organic (carbon-containing) substances or compounds are present in natural bodies of water, on organic substrates, and in organic wastes. The exact type of microorganisms present may vary greatly among different materials and conditions, yet each has the ability to degrade organic materials. The elemental nutrient requirements of microbes are approximately the same as the microbes' average elemental composition. The carbon, which makes up a majority of the microbes' composition, is obtained from the available organic compounds, such as sewage. However, the remaining elemental materials necessary for growth must be provided from the same organic compounds being degraded, the available water, a substrate, or a supplementary source. Potentially, the growth of the microbial population, in either amount or type of microorganism, can be limited by any shortage in the presence or supply of nutrients or the existence of conditions hostile to growth of the microbes. Consequently, the degradation of a targeted organic waste is directly effected by nutrient availability, as well as carbon, water, and oxygen availability. Furthermore, it is believed that use of the present compositions reduces the presence of pathogenic microbes, presumable due to greater competition from a healthy population of non-pathogenic microbes. It is further contemplated that the compositions enhance microbial biodegradation of the waste through a pathway that reduces the amount of odorous gases emitted.

In accordance with the invention, it has been found that the addition of nutrients to organic wastes may not be necessary to promote microbial growth, especially in certain applications wherein the organic wastes already have significant nutrient content. However, carboxylic acids, such as fatty acids, have been found to increase microbial growth and subsequent biodegradation of a wide range of organic waste products. The synergistic effect of combining a saturated and unsaturated fatty acid is a particularly beneficial result. It is believed that the microbes can utilize carboxylic acids more easily than other organic materials, such that the microbial population can grow large enough in number to better degrade the other organic materials. Furthermore, it is possible that the microbial population will change in type, such that microbial types, such as rotifers and protozoas, that are better suited to organic degradation are fostered.

In one embodiment, the composition or formulation includes a mixture of saturated and unsaturated fatty acids to form a composite that is readily biodegradable and has physical properties making it efficient for promoting microbial growth. More particularly, the fatty acids form an oleophilic and biodegradable composition comprising oleic acid and a carboxylic acid selected from stearic acid, palmitic acid, and mixtures thereof. The composition of the present invention may be prepared with any ratio of saturated fatty acids and unsaturated fatty acids. It is preferred for the composition to have a sufficiently high melting temperature to allow the material to be stored without clumping together. The preferred ratio of oleic acid (or any of the unsaturated fatty acids) to the saturated fatty acids is between about 70:30 and about 30:70 by weight, most preferably between 60:40 and 40:60 by weight. The most preferred fatty acids have between 14 and 20 carbon atoms.

While a combination of fatty acids may simply be mixed together to form a solid, a liquid or slurry, preferred compositions and preferred methods of making the compositions as a solid particle or powder are described in U.S. Pat. Nos. 5,443,845, 5,725,885 or 6,277,279, and each of these patents are incorporated by reference into this application. In a suitable method of preparing the composition, the fatty acids are mixed together, heated to melting, for example at 100 degrees Celsius, then cooled to produce a homogenous solid mixture.

When applying the fatty acids to coat other compounds, the coating mixture may be re-melted, for example at 100 degrees Celsius, to achieve a smooth flowing liquid, then cooled to about 65 degrees C., so that it will solidify quickly when applied to the other compounds. Accordingly, the particulate composite can be manufactured in at least two ways. Using a conventional manufacturing method, the coating material is added as a liquid into the dry solids mixer while the nutrients are being blended. An appropriate dry solids mixer for this method is a ribbon blender (available from Ross Manufacturing). It may be helpful to equip the ribbon blender with a chopper attachment to reduce clumps that form in the mixing process. In one embodiment, the coating formula is added to nutrients at a ratio of 10% by weight to ensure adequate encapsulation. The coated nutrient mixture must be removed from the mixer and passed through a U.S. standard number 20 sieve to remove clumped material. Preferably, the sifted material is then remixed with 1 to 1.5% amorphous silica or any other standard anti-caking agent to maintain the free flowing properties of the particles.

Whether or not nutrients, oxygen-releasing compounds or microbes are included, the composition is preferably manufactured either as a powder, pellet or particulate of varying size. A finely powdered material is preferred for use in chicken houses primarily for the practical reason that the chickens are unable to peck at it.

The exact application interval and dosage of the composition per unit area is based upon factors such as the degree of organic contamination, composition of the organic waste, type of bacteria present and microbial activity. It will be recognized that the composition may be applied in various manners and on various schedules, but as a practical matter it is preferred to apply the composition in a batch mode with an interval of one to two weeks between applications. Each application of the composition is preferably, but optionally, accompanied by the application of a sufficient quantity of water to moisten the composition. Application techniques include dry spreading followed by watering or, more preferably, mixing the composition in water and applying the aqueous mixture over the bedding. It is preferred to periodically rake, turn, agitate, or otherwise mix and aerate, the bedding, such as after each application of the composition.

While the carboxylic acids described herein, such as the fatty acids, may be used in any concentration that is effective to promote waste remediation or odor control, the carboxylic acids are preferably applied at a rate of between 0.025 and 0.6 pounds of the carboxylic acid composition per cubic yard of substrate being treated, particularly for chickens raised over a sawdust substrate, once every 1 to 3 weeks, most preferably at least once every 2 weeks. If nutrients, oxygen-containing compounds, microbes, or other additives are to be used in conjunction with the carboxylic acid composition, then these components will add to the weight of the total composition while the application rate of the carboxylic acids should remain in the stated range. It should also be recognized that the number of applications may be reduced by providing the compositions in a timed-release formulation that makes the composition available to microbes at the same rates described herein.

One exemplary treatment plan begins with applying 0.25 to 6 pounds, more preferably 0.25 to 2 pounds, of a coated nutrient composition (containing about 80 to 90 wt % nutrients, See Example 2) per cubic yard of bedding. Preferably, a similar amount of the coated nutrient composition is periodically reapplied, such as once every 1 to 3 weeks, most preferably at least once every 2 weeks until the bedding is discarded.

In one embodiment, the fatty acid composition may be mixed with compounds that provide a source of molecular oxygen including, but not limited to, calcium peroxide, magnesium peroxide, potassium peroxide, or urea hydrogen peroxide. Each of these compounds is capable of releasing molecular oxygen ($O_2$) by enzymatic or chemical reactions. This molecular oxygen is utilized by the microorganisms to enhance and promote aerobic metabolism throughout the waste environment rather than solely at an interface between the waste and the surrounding air. These oxygen-releasing compounds may be mixed with or coated with the fatty acid compositions described herein. When oxygen-releasing compounds are utilized, it is preferred that these compounds comprise between about 1 and about 20 percent (%) by weight of the fatty acids. However, because hydrogen peroxide, in particular, is known to be unstable in aqueous solutions and is also toxic to microorganisms at high concentrations, the oxygen releasing compounds of hydrogen peroxide are preferably incorporated as encapsulated particulates. Utilization of hydrogen peroxide and peroxide compounds to enhance microbial growth has been well documented, but has seen little practical application in the field because of problems of stability and toxicity. Encapsulating the particulate peroxide compounds serves to stabilize the materials by preventing the compounds from rapidly reacting with water or divalent cations (for example $Fe^{+2}$) that promote peroxide degradation. The encapsulation also prevents the toxicity of rapid peroxide decomposition from affecting the microorganisms by regulating the release of these compounds at concentrations that support microbial growth and limit promotion of toxic oxygen radicals.

When the fatty acid composition includes both nutrients and an oxygen-releasing compound, the oxygen-releasing compound may be incorporated into the nutrient formulation, into the fatty acid coating matrix, or both. Still, it is preferred that the oxygen releasing compounds comprise between about 1 and about 20 percent (%) by weight of either the nutrient formulation, the oleophilic coating, or both together.

It is believed that the oleophilic composition adheres to, or is disposed in contact with, the organic bedding substrate rather than being carried off by water. In this manner, the composition is retained on the substrate surface where the waste is disposed. Accordingly, all the necessary conditions for remediation converge at the substrate surface. Specifically, the microbes receive: carbon and certain nutrients from the animal waste; carbon, nutrients and physical support from the bedding substrate; oxygen from the air exposed to the high-surface-area substrate; water applied over the substrate and absorbed/adsorbed by the substrate from an external water source or the animal waste; and bio-available carbon from the oleophilic composition in the form of carboxylic acids, such as saturated and/or unsaturated fatty acids. Optionally, the oleophilic composition may also provide one or more nutrients and/or one or more sources of oxygen that enhance microbial growth. Additionally, the oleophilic composition may be provided as a liquid that is absorbed or adsorbed by the substrate rather than as a solid adhered or disposed on the surface of the substrate.

The present invention recognizes the contributions made by each of the materials available in the bedding layer and provides a composition that works in conjunction with those materials to provide a complete and robust environment for microbial growth and remediation of the waste. In particular, while the substrate and waste both provide sources of carbon, carboxylic acids, especially fatty acids, have been found to enhance and accelerate remediation. Therefore, all of the compositions of the present invention provide carboxylic acids. Depending upon the nutrients made available in the waste and the substrate, the composition may optionally include any necessary or beneficial nutrients, such as nitrogen, phosphorous, potassium and iron. However, by way of example, it is believe that chickens absorb only a minor portion of the nutrients ingested from their feed and that a significant amount of nitrogen, phosphorous, and potassium are excreted in their waste. Accordingly, it is typically unnecessary for any of the nutrients excreted in the waste to also be included in the composition, simply because these nutrients are already present in sufficient amounts. It is for this reason, that it is believed that carboxylic acids, such as fatty acids, alone will promote remediation of chicken waste without any further application of nutrients to the bedding. Even so, fatty acid compositions that include nutrients have been shown to be effective.

In one embodiment, a fatty acid composition includes a nutrient formulation. The preferred nutrient formulations for fostering the growth of waste degrading bacteria have the following exemplary proportions (the percentages here are based only on the weight of the nutrients, excluding any coating, oxygen-containing compounds, etc.):

between about 80 and about 90 percent (%) by weight of a source of nitrogen selected from ammonium sulfate $(NH_4)_2SO_4$, urea and combinations thereof;

between about 5 and about 8 percent (%) by weight potassium phosphate dibasic $K_2HPO_4$ or substitutions such as potassium phosphate monobasic $KH_2PO_4$ or calcium phosphate monobasic $CaHPO_4$, dibasic $Ca(H_2PO_4)_2$ or tribasic $Ca_3(PO_4)_2$, urea phosphate, or ammonium phosphate $NH_4H_2PO_4$; and between about 1 and about 2 percent (%) by weight ferrous sulfate $FeSO_4$ or a substitution such as ferrous sulfate heptahydrate $FeSO_4$*$7H_2O$.

A particularly preferred coated nutrient composition includes the following ingredients (the percentages here are based on the total weight of the coated nutrient composition):

Nutrients: 85 wt. % ammonium sulfate $[(NH_4)_2SO_4]$;

5 wt. % dry fertilizer (urea, diammonium phosphate, potassium chloride, limestone, dolomite limestone, ammonium sulfate, potassium sulfate, superphosphate, corncobs (pulverized), calcium lignosulfonate, mineral oil, sulfer); and 1 wt. % chelated iron The nutrients above are blended to pass a number 60 sieve before coating.

Coating: 7 wt % coating material (60 wt. % oleic acid; and 40 wt. % stearic acid)

Anticaking Agent: 2 wt. % synthetic amorphous silica.

The materials above are passed through a number 40 sieve before packaging or use.

The most preferred nutrient formulations have an ammonium/urea:phosphate-compound:iron compound ratio between about 90:8:2 and about 94:5:1. The precise formulation of nutrients can vary according to the specific type of microorganism present in the bedding (substrate, waste, water or the present composition), the composition of the waste products, and the current costs of each nutrient source. The nutrient formulation is mixed together as dry ingredients and ground into a powder sufficient to pass a U.S. standard number 40 sieve. It has also been found that a suitable source of iron is in the form of chelated iron.

The compositions of this invention work especially well at remediating and/or reducing odors of animal wastes, such as manure and urine, deposited on or in a substrate. However, the composition may also be effective in composting plant and/or animal waste. Furthermore, it is believed that the compositions described herein provide a beneficial effect in various microbial populations by increasing the population of certain desirable microbes and decreasing the population of pathogenic microbes. In recognition that many biological processes within a given environment may interact in a variety of manners, both known and unknown, the compositions may produce beneficial effects through various points of use. For example, because of the interrelatedness of the microbes in the bedding and the microbes in the digestive system of chickens due to the ingestion of bedding material, waste products or the present compositions, it may be possible to achieve similar results by including the compositions in the feed, drinking water, bedding, or some combination thereof. In either way, portions of the composition, waste and improved or changed microbial population will end up in both the bedding and the digestive system of the animal. It is possible that the composition changes the flora in the stomach of the chickens and reduces pathogenic microbes within the chickens as well as the amount of pathogenic microbes secreted through their fecal matter and urine.

The effectiveness of the fatty acids in promoting microbial degradation is shown in the following examples.

EXAMPLE 1

A test was performed to determine the relative performance of various additives on the bioremediation or degradation of wastes suspended in water. Measurements of the "biological oxygen demand" (BOD) and "total suspended solids" (TSS) were taken as representative of the progress of the microbial growth and effectiveness of the degradation brought about by the microbes.

Approximately five pounds of pig waste was collected from a feedlot and diluted in five gallons of deionized water. The mixture was allowed to sit for 24 hours to insure that the waste formed a uniform mixture. Five hundred milliliters (500 ml) of the aqueous waste mixture was added to each of 13 two-liter glass bottles that were closed with Teflon lined caps. Ammonium hydroxide was added to each container for a final concentration of 2000 ppm.

The samples were diluted with water 2:1 and filtered to remove large particulate matter. Various fatty acids and combinations of fatty acids were added to each bottle and the bottles were placed in a tumbler at 25 degrees Celsius. Seven of the bottles were used in a seven-day test and six of the bottles were used in a twelve-day test. Standard EPA test methods were used for all test measurements.

TABLE 1

| | | Seven-day test | | | |
|---|---|---|---|---|---|
| FATTY ACID | AMOUNT (grams) | BOD (ppm) | TSS (ppm) | PLATE COUNT (per 100 ml) | APPEARANCE |
| Strearic | 0.1 | — | 16,080 | — | Darkened |
| Lauric | 0.1 | — | 16,040 | — | — |
| Linoleic | 0.1 | — | 15,780 | — | Darkened |
| Oleic | 0.1 | — | 15,600 | — | Darkened |
| Corn Oil | 0.1 | — | 15,890 | — | — |
| Coated Nutrient | 0.5 | — | 15,660 | — | Darkened |
| Blank | 0.0 | — | 16,070 | — | — |

BOD (biological oxygen demand) and TSS (total suspended solids) were measured on each sample. The sample treated with stearic acid alone showed a 9.5% BOD reduction and a 10.0% TSS reduction. The sample treated with oleic acid showed a 13.0% BOD reduction and a TSS reduction of 19.6%. The sample treated with linoleic acid alone showed a 12.2% reduction in BOD and a 13.3% reduction in TSS.

The samples treated with a linoleic/stearic (unsaturated/saturated) combination of fatty acids showed a BOD reduction of 31.0% and a TSS reduction of 35.0%. The samples treated with an oleic/stearic (again unsaturated/saturated) combination of fatty acids showed a BOD reduction of 28.6% and a TSS reduction of 29.5%.

It is interesting to note that while each of stearic acid, oleic acid and linoleic acid yielded BOD levels of 6660, 6050 and 6102 ppm and TSS levels of 455, 407 and 439, respectively, the combinations of linoleic/stearic and oleic/stearic yeilded BOD levels of 4800 and 4960 (an average BOD reduction of 22% greater than with the component fatty acids) and TSS level of 328 and 379 (an average TSS reduction of 18.7% greater than with the component fatty acids), respectively. This indicates that the two combinations of saturated and unsaturated fatty acids have a statistically significant positive effect on the reduction of organic waste with high ammonia concentrations. Furthermore, these results suggest that there is a synergistic effect provided when a saturated and unsaturated fatty acid are used in combination.

EXAMPLE 2

A fatty acid coating material was prepared by mixing 60 wt. % oleic acid and 40 wt. % stearic acid, heating the mixture to melting at 100 degrees Celsius, then cooling the material to produce a homogenous solid mixture.

A nutrient formulation was separately prepared by mixing together 85 wt. % (based on the total composition) ammonium sulfate [$(NH_4)_2SO_4$], 5 wt. % dry fertilizer (urea, diammonium phosphate, potassium chloride, limestone, dolomite limestone, ammonium sulfate, potassium sulfate, superphosphate, pulverized corncobs, calcium lignosulfonate, mineral oil, sulfur), and 1 wt. % chelated iron. These nutrients were blended to pass a number 60 sieve before coating.

The fatty acid coating material was re-melted at 100 degrees Celsius, to achieve a smooth flowing liquid, then cooled to about 65 degrees Celsius, so that it would solidify quickly when applied to the nutrients. The coating material was added to the nutrients as a liquid into a dry solids mixer while the nutrients were being blended so that the coating material would account for 7 wt % of the final composition. The coated nutrient mixture was then removed from the mixer and passed through a U.S. standard number 20 sieve to remove clumped material.

After cooling, 2 wt. % synthetic amorphous silica anticaking agent was mixed with the coated nutrient composition. This entire material was then passed through a number 40 sieve before use.

EXAMPLE 3

A chicken house using sawdust as a bedding substrate had a history of chicken mortality of about 1900-2400 per group of 30,000 chicks hatched. This represented between about 6.3 and 8.0 percent mortality over a six-week period following hatching. It was also typical for the chickens' legs to turn from yellow to white.

A new set of 30,000 recently-hatched chicks were grown for six weeks over a six-inch thick bed of sawdust in a commercial chicken house. After a period of two weeks, the coated nutrient composition of Example 2 was spread with a manual fertilizer spreader at a rate of 0.25 pounds of the coated nutrient composition per cubic yard of sawdust. The sawdust was then sprayed with water until the bedding was moist. The bedding was then manually raked to aerate and mix the sawdust and the coated nutrient composition.

On the fourth day after applying the composition, the typical ammonia smell associated with chicken waste accumulation on the sawdust was eliminated. The bedding was raked once each week and an additional 0.25 pounds of the composition per cubic yard of sawdust was applied every two weeks. It was observed that the treated bedding experienced much less crusting than untreated bedding under similar conditions.

It was also noted that the chickens' legs remained a healthy yellow color each week, instead of turning white as was previously typical. Furthermore, the number of chickens that died each week declined each week throughout the six-week period that the chickens remained on the bedding. At the end of six weeks, a total of only 230 chickens had died. These 230 chickens represent a mortality rate of only about 0.8 percent of the original 30,000 chicks—almost a factor of ten less than the mortality rate experienced when the sawdust was not treated.

EXAMPLE 4

The experiment of Example 3 was repeated except that the composition of Example 2 was applied with a paint sprayer. Two pounds of the coated nutrient composition was mixed with about 2.5 gallons of water. The mixture was sprayed over about 8 cubic yards of sawdust bedding, which treated an approximately six inch thick bed of sawdust spread over an area of 432 square feet. After the application, the sawdust was raked for aeration and mixing.

EXAMPLE 5

The experiment of Example 4 was repeated except that the mixture was applied over the sawdust bedding after the chickens were already six weeks old and the odor from the bedding was very strong. By the fifth day after the application and until the chickens were harvested at eight weeks old, the odor was almost undetectable.

The composition and method of the invention was shown to affected avian performance in the following manner: (i) improving weight gain and feed efficiency, resulting in an improved weight adjusted feed efficiency; (ii) lowering disease exposure to the avian, (iii) improving avian health; and (iv) reducing odors within an avian house.

EXAMPLE 6

The coated nutrient composition of Example 2 was applied at a rate of 0.25 pounds per cubic yard of bedding in one half of a chicken house. The chicks were kept in this half of the house for about one to two weeks. Then, 0.25 pounds of the composition per cubic yard of bedding was applied throughout the entire house, and the whole house was opened to the chickens. The composition was reapplied at a similar rate to all of the bedding in the chicken house every 2 weeks until the chickens were harvested.

It is believed that the composition and method of the invention will allow the use of a bedding substrate to be extended, such as allowing a second set of chicks to be grown and harvested before discarding the bedding material. Furthermore, using the composition and method produces used bedding that is suitable as a fertilizer for a garden or crops.

Important Definitions:

The term "avian" means any warm-blooded, egg-laying, feathered vertebrate provided with wings and is used generally synonymous with the term "poultry."

The term "avian house" or "chicken house" means any building used to house or shelter poultry for any reason (synonymous with hen house, chicken coop, coop, hen coop, grow out barn, and breeder house).

The term "bedding" or "animal bedding" means any material or covering used to provide a bed for animals to deposit their waste on. Examples of bedding include wood shavings/chips, sawdust, rice hulls, and straw.

The term "carboxylic acid" means any of a family of organic acids characterized by the presence of one or more carboxyl groups (—COOH).

The term "improved avian performance" means any improvement in an economic parameter used to determine improved revenues from the sale or barter of avian products for retail sale. For example, live body weight, carcass weight, salable meat yield, salable eggs, feed efficiency, average daily gain, eggs per hen housed, viable chicks, chicks per hen housed etceteras.

The terms "microbes" and "microorganisms," as used herein, are used interchangeably and are intended to be synonymous.

The term "organic" refers to compounds that are based on carbon chains (straight or branched) or rings and also containing hydrogen with or without oxygen, nitrogen, or other elements.

The term "poultry" means any domestic fowl reared for the table, or their eggs or feathers including broilers, fryers, cocks and hens, capons, turkeys, ducks, geese and any others.

The term "reducing" means lessening the intensity, duration, and offensiveness of an odor or smell such that the odor or smell is at least marginally eliminated.

The term "applying" is defined herein broadly to mean spraying, dispersing, scattering, mixing, blending, combining, stirring, merging, mingling, or any other method of placing the odor reducing composition in contact with the odorous substrate.

The term "substrate" is herein defined as any solid material that forms a porous bedding material. Examples of substrates include organic solids such as hay, straw, grass and manure or fecal matter; and inorganic materials such as soil. Often, the organic and inorganic substrates are mixed or blended. These organic or inorganic substrates are found in places such as barns, stables, chicken coops, pig sties, fairgrounds, dog pounds, pet clinics, animal laboratories, zoos, or any other area occupied by livestock or other animals and contaminated by manure, or fecal matter, and/or urine.

The term "fatty acid" includes both saturated and unsaturated fatty acids. The term "saturated fatty acid" means an organic acid, typically monobasic, of the general formula $C_nH_{2n+1}COOH$ derived from the saturated series of aliphatic hydrocarbons; examples are palmitic acid, stearic acid and oleic acid. The term "unsaturated fatty acid" means an organic acid similar to a saturated fatty acid, except that it is has more than one bond (for example, a double bond) between adjacent atoms, usually carbon.

The terms "comprising," "including," and "having," as used in the claims and specification herein, shall be considered as indicating an open group that may include other elements not specified. The term "consisting essentially of," as used in the claims and specification herein, shall be considered as indicating a partially open group that may include other elements not specified, so long as those other elements do not materially alter the basic and novel characteristics of the claimed invention. The terms "a," "an," and the singular forms of words shall be taken to include the plural form of the same words, such that the terms mean that one or more of something is provided. For example, the phrase "a solution comprising a phosphorus-containing compound" should be read to describe a solution having one or more phosphorus-containing compound. The term "one" or "single" shall be used to indicate that one and only one of something is intended. Similarly, other specific integer values, such as "two," are used when a specific number of things is intended. The terms "preferably," "preferred," "prefer," "optionally," "may," and similar terms are used to indicate that an item, condition or step being referred to is an optional (not required) feature of the invention.

It should be understood from the foregoing description that various modifications and changes may be made in the preferred embodiments of the present invention without departing from its true spirit. Accordingly, the foregoing description is for purposes of illustration only and should not be construed in a limiting sense. Only the language of the following claims should limit the scope of this invention.

What is claimed is:

1. A method for treating animal bedding waste, comprising:

in situ application to an animal bedding material between about 0.25 and about 6 pounds of a composition per cubic yard of the animal bedding material, wherein the composition comprises ferrous sulfate, chelated iron and at least 5 weight percent of a combination of saturated and unsaturated fatty acids having from 12 to 22 carbon atoms.

2. The method of claim 1, wherein between about 0.025 and about 2 pounds of the composition is applied for each cubic yard of the substrate every 1 to 3 weeks.

3. The method of claim 1, wherein the fatty acids include at least one saturated fatty acid selected from stearic acid, palmitic acid and mixtures thereof.

4. The method of claim 1, wherein the fatty acids include at least one unsaturated fatty acid selected from oleic acid, linoleic acid and mixtures thereof.

5. The method of claim 1, wherein the saturated and unsaturated fatty acids are combined at a ratio between 70:30 and 30:70 by weight.

6. The method of claim 5, wherein the saturated fatty acids include stearic acid and the unsaturated fatty acids include oleic acid.

7. The method of claim 5, further comprising at least 1 weight percent of an amine-substituted form of a fatty acid.

8. The method of claim 1, further comprising:

moistening the bedding with water.

9. The method of claim 1, wherein the composition is a powder.

10. The method of claim 1, wherein the composition forms pellets, powder, granules, or cakes.

11. The method of claim 5, wherein the saturated fatty acids consist essentially of stearic acid and the unsaturated fatty acids consist essentially of oleic acid, linoleic acid, or a combination thereof.

12. The method of claim 5, wherein the ratio of the one or more saturated fatty acids to the one or more unsaturated fatty acid is between about 60:40 and 40:60 by weight.

13. The method of claim 1, wherein the one or more fatty acids are solids at ambient temperatures.

14. The method of claim 5, wherein the one or more fatty acids are solids at ambient temperatures.

15. The method of claim 14, wherein the solids are in the form of pellets, powder, granules, or cakes.

16. The method of claim 1, wherein the animal bedding is selected from sawdust, wood chips, wood shavings, straw, and sand.

17. The method of claim 1, wherein the composition further comprises a source of molecular oxygen.

18. The method of claim 17, wherein the source of molecular oxygen is selected from calcium peroxide, hydrogen peroxide, urea hydrogen peroxide, sodium percarbonate, potassium peroxide, and magnesium peroxide.

19. The method of claim 12, wherein the step of applying the composition to the bedding occurs without adding a separate source of nitrogen or phosphorous.

20. The method of claim 17, wherein the source of molecular oxygen comprises between about 1 and 20 percent by weight of the one or more fatty acids.

21. The method of claim 15, wherein between about 0.1 and about 2 weight percent of amorphous silica is mixed with the composition to prevent clumping.

22. The method of claim 1, wherein the fatty acids have from 16 to 20 carbon atoms.

23. The method of claim 1, wherein each application of the composition includes between 0.025 and 0.6 pounds of carboxylic acids per cubic yard of substrate.

24. The method of claim 1, wherein the ferrous sulfate comprises between about 1 and about 2 percent (%) by weight of the composition.

25. The method of claim 24, wherein the composition further comprises between about 80 and about 90 percent by weight of a source of nitrogen selected from the group consisting of ammonium sulfate, urea and combinations thereof.

26. The method of claim 25, wherein the composition further comprises between about 5 and about 8 percent by weight of a compound selected from the group consisting of potassium phosphate dibasic, potassium phosphate monobasic, calcium phosphate monobasic, calcium phosphate dibasic, calcium phosphate tribasic, urea phosphate, ammonium phosphate, and combinations thereof.

27. The method of claim 1, wherein the ferrous sulfate comprises between about 1 and about 2 percent (%) by weight of the composition.

28. The method of claim 1, wherein the ferrous sulfate is ferrous sulfate heptahydrate.

29. A method for treating animal bedding waste, comprising:

in situ application of a composition including saturated and unsaturated fatty acids having from 12 to 22 carbon atoms, chelated iron and ferrous sulfate to an animal bedding material, wherein the composition is applied in an amount that is effective to enhance remediation of animal waste within the bedding material.

30. The method of claim 29, wherein the amount of the composition is also effective to reduce odors from the animal bedding waste.

31. The method of claim 29, wherein the fatty acids have from 16 to 20 carbon atoms.

32. The method of claim 29, wherein the ferrous sulfate is ferrous sulfate heptahydrate.

* * * * *